United States Patent [19]

Iwamoto et al.

[11] 4,360,269
[45] Nov. 23, 1982

[54] APPARATUS FOR INSPECTING DEFECTS IN A PERIODIC PATTERN

[75] Inventors: Akito Iwamoto, Kamakura; Hidekazu Sekizawa, Yokohama, both of Japan

[73] Assignee: Tokyo Shibaura Denki Kabushiki Kaisha, Kanagawa, Japan

[21] Appl. No.: 202,320

[22] Filed: Oct. 30, 1980

[30] Foreign Application Priority Data

Nov. 7, 1979 [JP] Japan ............................ 54/143228

[51] Int. Cl.$^3$ .......................................... G01N 21/00
[52] U.S. Cl. ............................. 356/239; 350/162 SF
[58] Field of Search ............... 350/162 SF; 356/237, 356/239; 250/550

[56] References Cited

U.S. PATENT DOCUMENTS 3,614,232 10/1971 Mathisen ..................... 356/237 X
3,790,280 2/1974 Heimz et al. ................. 356/239 X

OTHER PUBLICATIONS

Iwamoto et al., "Rotation-, Shift-, and Magnification-Insensitive Periodic Pattern-Defects Optical Detection System", Applied Optics, vol. 19, No. 7, pp. 1146-1200, Apr. 1980.
Konowa Ichuk et al., "A Rapid Method for Assessing the Quality of Sieves", Powder Technology, vol. 13, No. 1, pp. 97-101, Feb. 1976.
Will et al., "Filtering of Defects in Integrated Circuits with Orientation Independence", Applied Optics, vol. 10, No. 9, pp. 2097-2100, Sep. 1971.
Watkins, "Inspection of Integrated Circuit Photomasks with Intensity Spatial Filters", Proc. IEEE, pp. 1634-1639, Sep. 1969.
Proceedings of the IEEE, Apr. 1972, pp. 447-448, "Intensity Spatial Filtering Applied to Defect Detection in Integrated Circuit Photo Masks" by Norman N. Axelrod.

Primary Examiner—John K. Corbin
Assistant Examiner—Matthew W. Koren
Attorney, Agent, or Firm—Schuyler, Banner, Birch, McKie & Beckett

[57] ABSTRACT

The apparatus of this invention is used for inspecting defects in a periodic pattern. The apparatus comprises a device for forming a Fourier transformed pattern of the periodic pattern and a filter for passing predetermined spatial frequency ranges of the Fourier transformed pattern. The predetermined spatial frequency ranges are lower than a spatial frequency which coincides with a first order diffraction of the Fourier transformed pattern.

9 Claims, 18 Drawing Figures

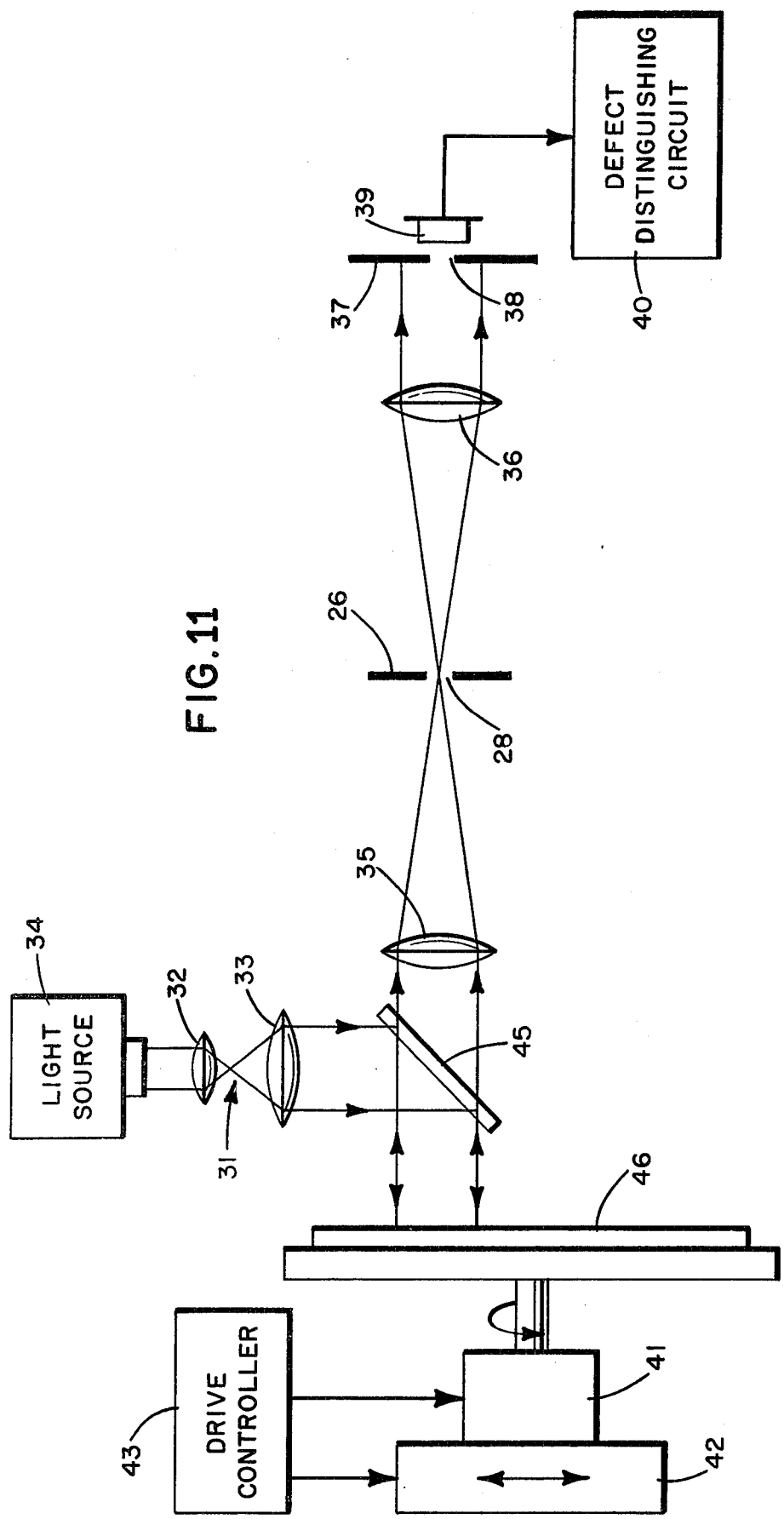

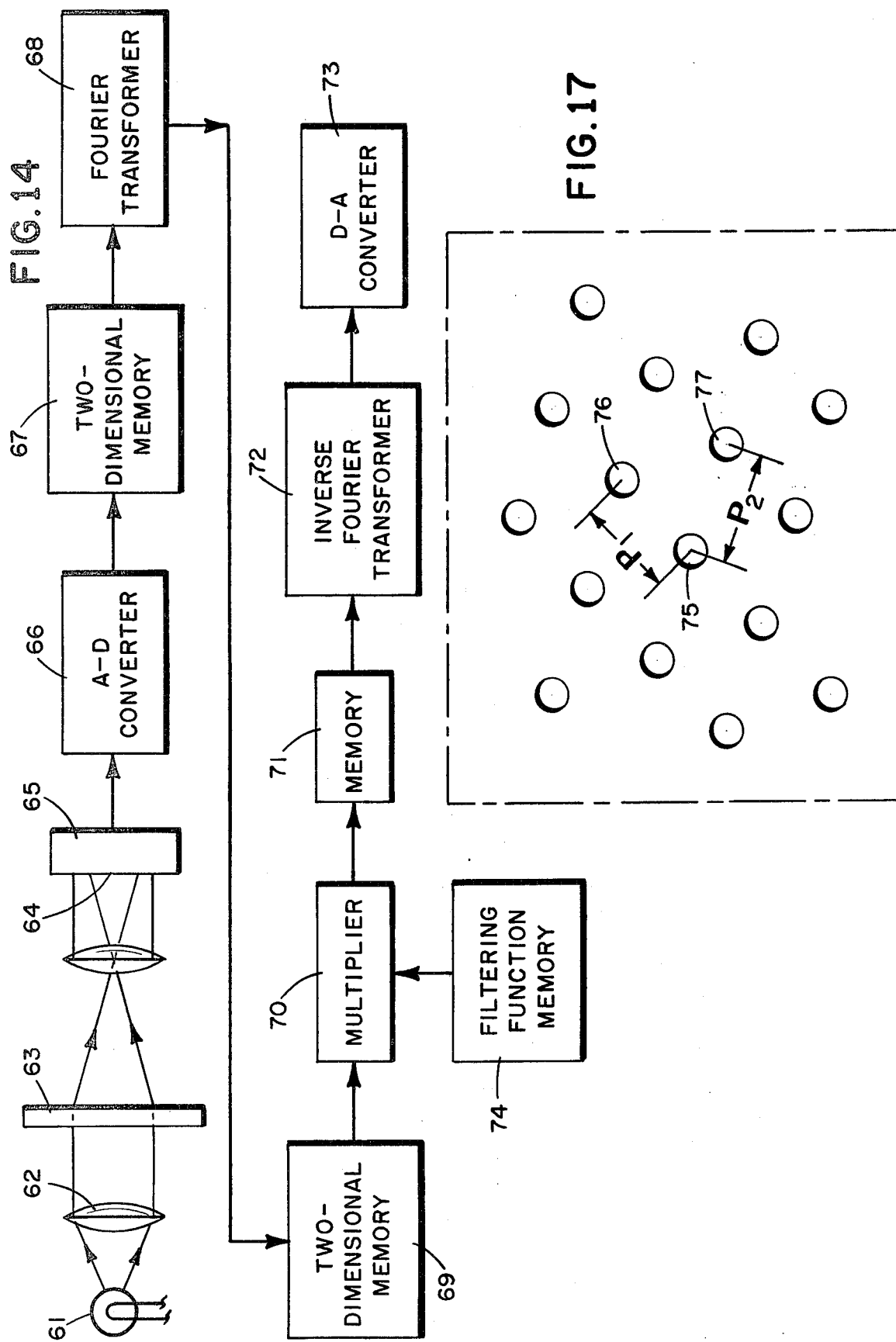

APPARATUS FOR INSPECTING DEFECTS IN A PERIODIC PATTERN

BACKGROUND OF THE INVENTION

The present invention relates to an apparatus for inspecting defects in a periodic pattern.

In conventional apparatus for inspecting defects in a periodic pattern, the pattern is visually examined with a microscope. Since, visual examination is inherently inaccurate, another well known inspection technique employs the combination of coherent light rays and a spatial filter. In this inspection technique, the optical information of the periodic pattern is separated into periodic pattern information and non-periodic pattern information by Fourier transformation and the non-periodic pattern information is examined by blocking the periodic pattern information with a spatial filter. This technique is disclosed in two articles in Proceedings of the IEEE, September 1969, pp. 1634 to 1639, "Inspection of Integrated Circuit Photomasks with Intensity Spatial Filters" by Watkins, and April 1972, pp. 447 to 448, "Intensity Spatial Filtering Applied to Defect Detection in Integrated Circuit Photomasks" by Axelrod. Also in U.S. patent application Ser. No. 130,370, filed Mar. 14, 1980, the above named inventor describes an improved apparatus using this inspection technique having on omni-directional spatial filter. A disadvantage of this technique is that the spatial filter and the examined pattern must be precisely aligned or oriented with each other.

All the above inspecting apparatus also have the disadvantage that it is impossible to distinguish between an enlarged hole defect and a reduced hole defect. For example, a mesh plate with a number of periodic square holes may have one kind of defect which is an enlarged hole as shown in FIG. 1A and another kind of defect which is a reduced hole as shown in FIG. 1B. The inspection apparatus detects defects by solving the formula $D^2=(E-P)^2$ where E is light information from the examined mesh plate pattern, P is light information from an ideal periodic pattern and D is light information representing defects. When the defect is an enlarged hole, $E>P$ and when the defect is a reduced hole, $E<P$. Accordingly, the prior art inspection apparatus cannot distinguish between the enlarged hole of FIG. 1A and the reduced hole of FIG. 1B.

Sometimes it is necessary to distinguish between an enlarged hole and a reduced hole. For example, the mesh plate with a reduced hole shown in FIG. 1B can be repaired by manually removing the intruding part 10 to thereby improve the yield. Also, there is sometimes a difference in the acceptable tolerance between an enlarged hole and a reduced hole.

SUMMARY OF THE INVENTION

It is one object of this invention to provide a new and improved apparatus for inspecting defects in a periodic pattern.

It is another object of this invention to provide an apparatus for inspecting defects in a periodic pattern which can distinguish between an enlarged hole defect and a reduced hole defect.

It is another object of this invention to provide an apparatus for inspecting defects in a periodic pattern which has a relatively large tolerance between the relative positioning and orientation of a periodic pattern and the optical elements of the apparatus.

It is a further object of this invention to provide an apparatus for inspecting defects in a periodic pattern which operates at a high speed.

According to the invention, there is provided an apparatus for inspecting defects in a periodic pattern. The apparatus includes a device for forming a Fourier transformed pattern of the periodic pattern. A filter is then provided for passing predetermined spatial frequency ranges of the Fourier transformed pattern, the predetermined spatial frequency ranges being lower than a spatial frequency which coincides with a first order diffraction of the Fourier transformed pattern.

BRIEF DESCRIPTION OF THE DRAWINGS

Other objects and features of the invention will become apparent to those skilled in the art from the following description of a prefered embodiment of the invention, as illustrated in the accompanying drawings, in which:

FIG. 11 shows a schematic diagram of another embodiment of the invention;

FIG. 14 shows a schematic diagram of another embodiment of the invention;

FIG. 17 illustrates another example of the periodic pattern.

DESCRIPTION OF THE PREFERRED EMBODIMENT

In the specification, the term "defect" means any factor which distorts a periodic pattern such as a different size pattern, deformation of the pattern, scratches on the pattern, dust stuck to the pattern, etc. The defect inspection apparatus according to the invention is used to detect such defects in the periodic pattern.

A mesh plate with a mesh pattern generally is formed in a vidicon or shadow mask of a color cathode ray tube for use as an object to be inspected. Such an object, however, is not limited to a mesh plate but may be an opaque object with a periodic pattern, for example, such as used in semiconductor products.

Figure 2:
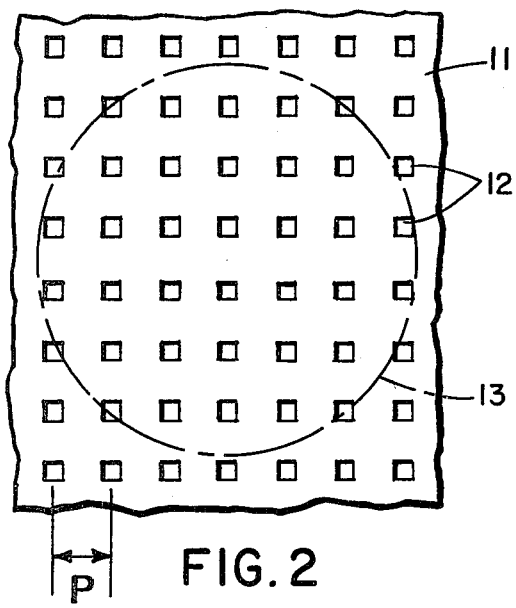
FIG. 2 shows a plan view of a mesh plate with a number of square holes as an example of a periodic pattern.
Figure 3:
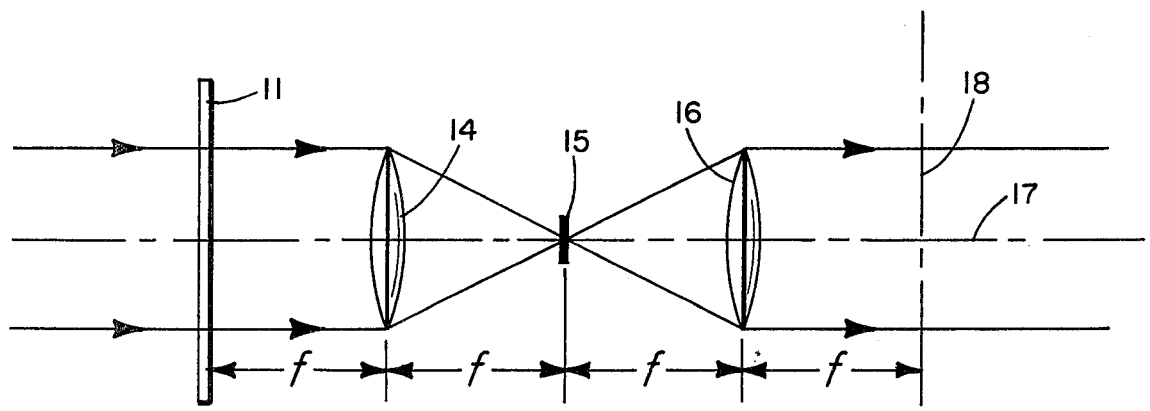
FIG. 3 shows a schematic view of the invention.

The basic concept of the invention will now be described referring to FIGS. 2 to 7. In FIG. 2, a mesh plate 11 is shown with a number of periodically arranged square holes 12. As shown in FIGS. 2 and 3, the mesh plate 11 is illuminated by a coherent light beam 13. A lens 14, a spatial filter 15, and a lens 16 are positioned in order on an optical path 17 of the beam 13, the spatial filter 15 being positioned at the focal point of lenses 14 and 16. Lens 14 forms a spatial Fourier transformer and lens 16 forms the inverse spatial Fourier transformer.

Figure 4:
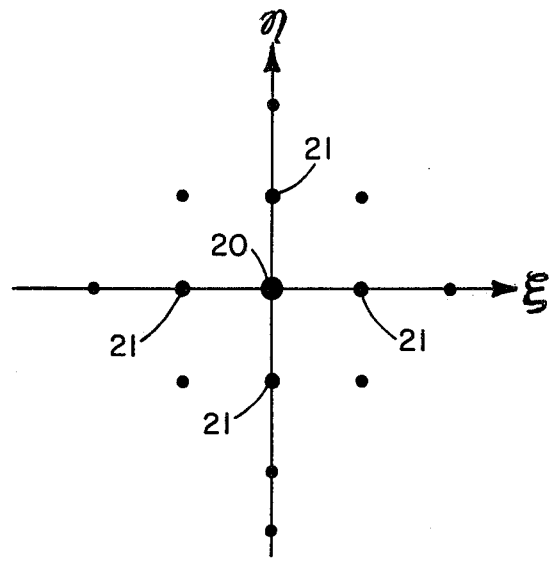
FIG. 4 shows a plan view of a diffraction pattern obtained by Fourier transformation of the periodic pattern shown in FIG. 2.

When coherent light beam 13 impinges upon mesh plate 11 with holes 12, the light beam from the pattern is Fourier transformed by lens 14 to form a diffraction pattern at the back focal plane of lens 14, namely at the position of spatial filter 15, as shown in FIG. 3. In the diffraction pattern, with the orthogonal coordinate system having $\xi$ and $\eta$ axes, a zeroth order defraction light component is directed to the origin to form a zeroth order spot 20, first order defraction light components are directed outside of the zeroth order spot 20 to form first order spots 21. In this way, second and higher order defraction light components are similarly directed to an area further outside of the preceeding order spots. The light intensity distribution of these diffraction light components on the $\xi$ axis of FIG. 4 is generally illustrated by a solid line A in FIG. 5. In FIG. 4, the spot size of each diffraction light component indicates the intensity of light.

The size of the diffraction areas and the distance between the diffraction areas is as follows. "P" denotes the pitch of the mesh pattern 18, i.e., the interval between the adjacent holes 12, and "N" denotes the number of holes 12 within the circle as counted in the direction of the pitch (N=6 in FIG. 2). Then, as shown in FIG. 5, the diameter of zeroth order diffraction area 20 is $2\lambda f/NP$ and the distance between zeroth order diffraction area 20 and first order diffraction area 21 is $\lambda f/P(1-2/N)$, where $\lambda$ is the wavelength of the coherent light projected and f is the focal length of the lens.

Figure 5:
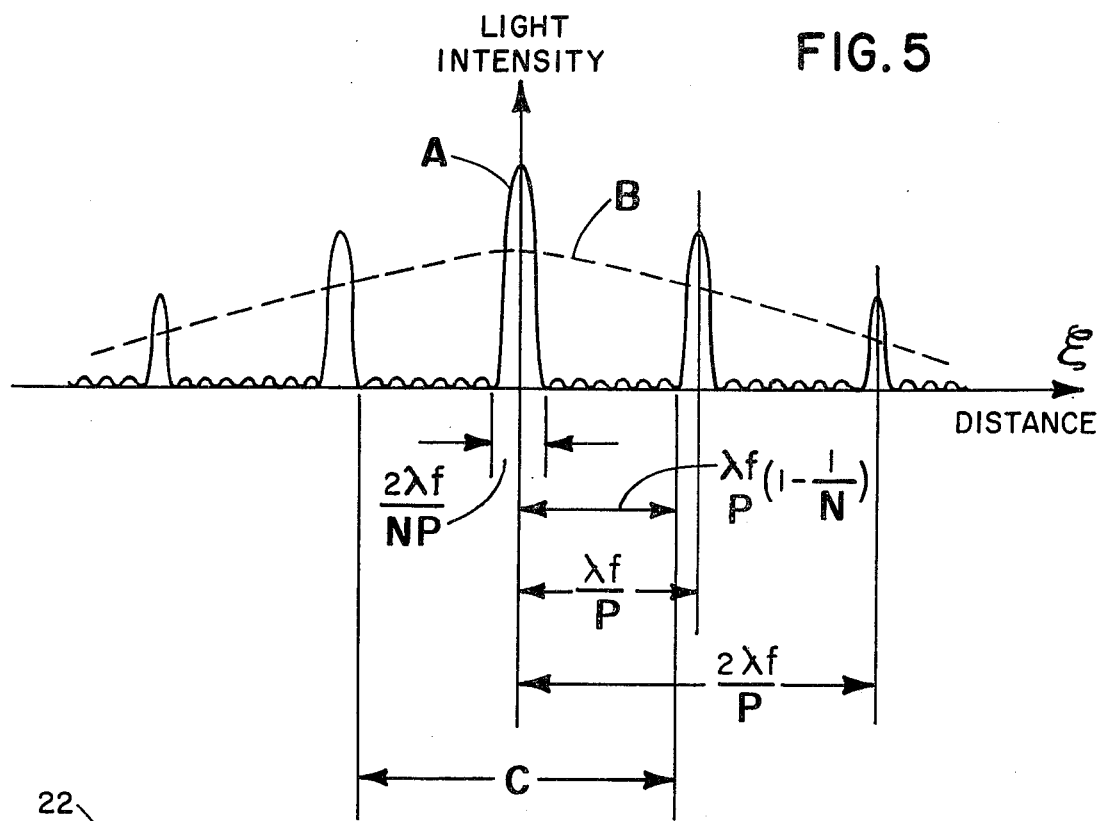
FIG. 5 shows a diffraction light intensity distribution of the image shown in FIG. 4.
Figures 6, 7:
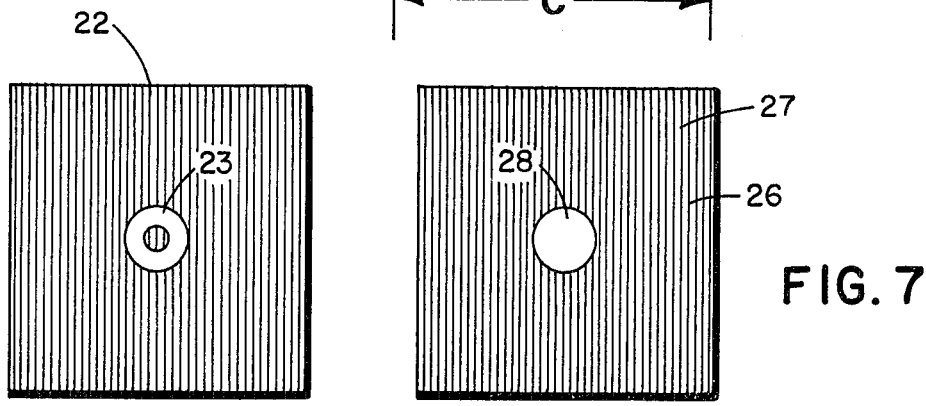
FIG. 6 shows a spatial filter of the defect inspection apparatus according to the invention of the above mentioned prior application Ser. No. 130,370.
FIG. 7 shows an example of a spatial filter of the defect inspection apparatus according to the present invention.

The diffraction pattern as shown in FIGS. 4 and 5 is periodic and is determined by the hole pattern in mesh plate 11. If a hole 12 has a defect as shown FIG. 1A, the defect diffracted pattern is given by a dotted line B in FIG. 5. Therefore, if a spatial filter is used to filter out the periodic diffraction pattern, e.g., a spatial filter 22 having a ring-like transmission area 23 as shown in FIG. 6, the non-periodic pattern represents the defect, namely, only the defect information may be extracted from the diffracted pattern in FIG. 4. For example, if spatial filter 22 is placed at the position 15 shown FIG. 3, a mesh pattern having only defect information light is obtained at the back focal plane 18 of lens 16.

However, as stated above, by extracting only the defect information, it is impossible to distinguish an enlarged hole defect and a reduced hole defect. The primary feature of the present invention is to extract not only the non-periodic pattern information component but also the zeroth order diffraction component, which is one of the periodic pattern information components.

If light information caused by an ideal periodic pattern P comprises a direct current component of light information L and a higher frequency component of light information H, light information caused by the examined mesh plate pattern E can be described as $E=H+L+D$ which can be rewritten as $L+D=E-H$, where $(L+D)^2 = L^2 + D^2 + 2LD$.

In the above formula, the value of 2LD is different in case of $D>O$ and $D<O$. Therefore, it is possible to distinguish between an enlarged hole defect shown in FIG. 1A and a reduced hole defect shown in FIG. 1B by examining the light intensity of light information, i.e., of the direct current component, caused by an ideal periodic pattern and light information caused by defects.

Figure 1A:
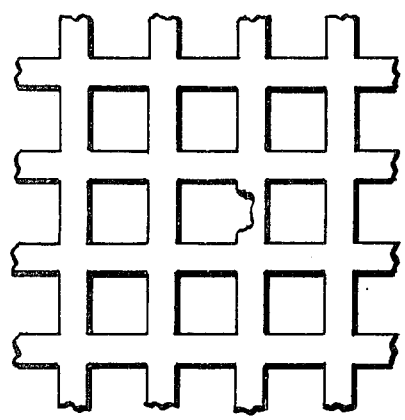
FIG. 1A shows a plan view of a mesh plate with a number of periodic square holes and an enlarged hole as an example of a periodic pattern with an enlarged hole defect.
Figure 1B:
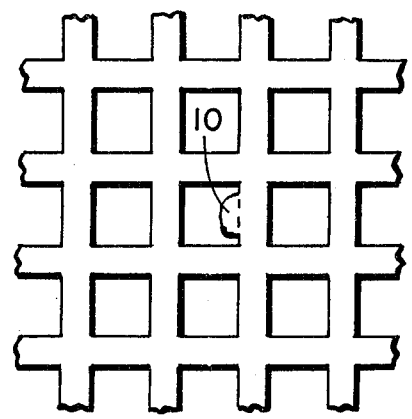
FIG. 1B is a plan view of a mesh plate with a number of periodic square holes and a reduced hole as an example of a periodic pattern with a reduced hole defect.

The light intensity $(L+D)^2$ is detected by a spatial filter 26 as shown in FIG. 7. Spatial filter 26 comprises a light blocking area 27 and a circular light transmission area 28. Circular light transmission area 28 is a circular hole having diameter C as shown in FIG. 5, i.e., $2\lambda f/P(1-1/N)$. Therefore, if spatial filter 26 is placed at the position 15 shown FIG. 3, a mesh pattern is obtained having defect information at the back focal plane 18 of lens 16. The enlarged hole defect shown in FIG. 1A is detected as a bright spot and the reduced hole defect shown in FIG. 1B is detected as a dark spot in the mesh pattern.

Figure 8:
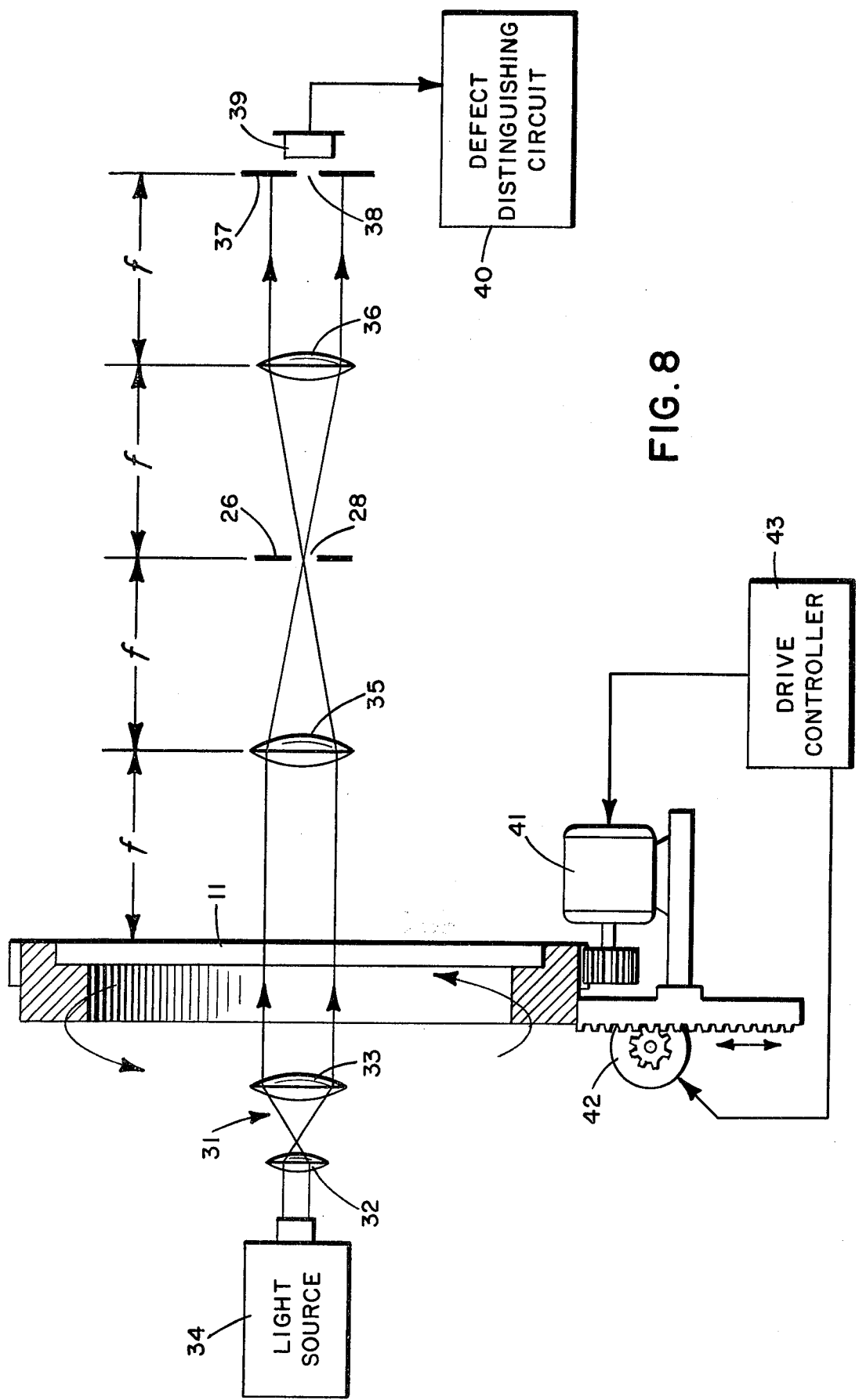
FIG. 8 is a schematic diagram of the defect inspection apparatus of the invention.

In FIG. 8, an embodiment of the defect inspection apparatus according to the invention is shown. A collimator 31 including lenses 32 and 33 is disposed on an optical path of a coherent light beam emitted from a light source 34, such as a laser device which generates a coherent light beam with a single wavelength. Collimator 31 converts the coherent light beam into parallel pencil light rays or a parallel light beam. A mesh plate 11, having a number of holes of identical shape arranged periodically thereon, is disposed on the optical path of the light beam for the purpose of inspection. A lens 35 disposed on the light path of the light beam transmitted through mesh plate 11 performs a spatial Fourier transformation of the light beam. Spatial filter 26 shown in FIG. 7 is located at the backward focal point of the lens 35 at which the Fourier transformed pattern of the periodic hole pattern is formed.

As above mentioned, the coherent light beam transmitted through mesh plate 11 includes light information on the periodic pattern and any defects, namely, it includes the periodic pattern information light component and the non-periodic pattern (defect) information light component. The periodic pattern information light component comprises the zeroth order diffraction light and first and higher order diffraction light. Light blocking area 27 of spatial filter 26 prevents transmission of the first and higher order diffraction light and circular light transmission area 28 of spatial filter 26 passes the defect information light component and the zeroth order diffraction light.

The light passed through spatial filter 26 is inverse Fourier transformed by lens 36 located at the focal distance f from spatial filter 26. A screen 37 with a pinhole 38 and photo-electric converter 39 is located at the backward focal point of lens 36. The light passed through lens 36 and pinhole 38 is received by photo-electric converter 39 and converted into electrical signals which correspond to the intensity of the light. The electrical signals are supplied to a defect distinguishing circuit 40 which distinguishes the kind of defect in mesh plate 11 by detecting the amplitude of the electrical signals from photo-electric converter 39.

Figure 9:
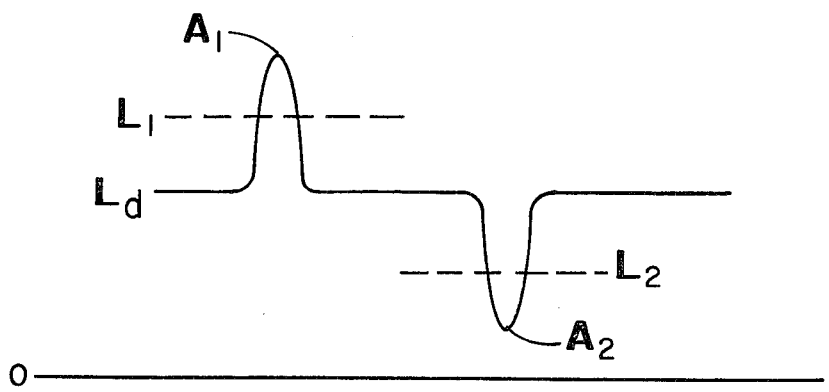
FIG. 9 shows waveforms obtained by photo-electric converter 39 shown in FIG. 8.

FIG. 9 shows an example of the electrical signal waveform from photo-electric converter 39. The electrical signal contains a direct current component Ld because spatial filter 26 passes the zeroth order diffraction light. When the part of mesh plate 11 which contains an enlarged hole defect is illuminated by the coherent light beam, the amplitude of the electrical signal increases as shown by A1 in FIG. 9. On the other hand, when the part of mesh plate 11 which contains a reduced hole defect is illuminated by the coherent light beam, the amplitude of the electrical signal is small as shown by A2 in FIG. 9. Therefore, defect distinguishing circuit 40 can distinguish the kind of defect in mesh plate 11 by comparing the amplitude of the electrical signals with two predetermined levels L1 and L2. Predetermined level L1 is higher than direct current component level Ld. Predetermined level L2 is lower than Ld.

Mesh plate 11 is supported by rotating mechanism 41 which rotates mesh plate 11 in a plane normal to the optical path of the optical system. Rotating mechanism 41 is further supported by a shifting mechanism 42 which shifts the mechanism at a constant rate in the plane of rotation. A drive controller 43 controls rotating mechanism 41 and shifting mechanism 42. Mesh plate 11 is laterally shifted in a direction orthogonal to the optical path of the coherent light beam, while being rotated in a plane normal to the optical path of the coherent light beam so mesh plate 11 is helically scanned by the coherent light beam.

Figure 10:
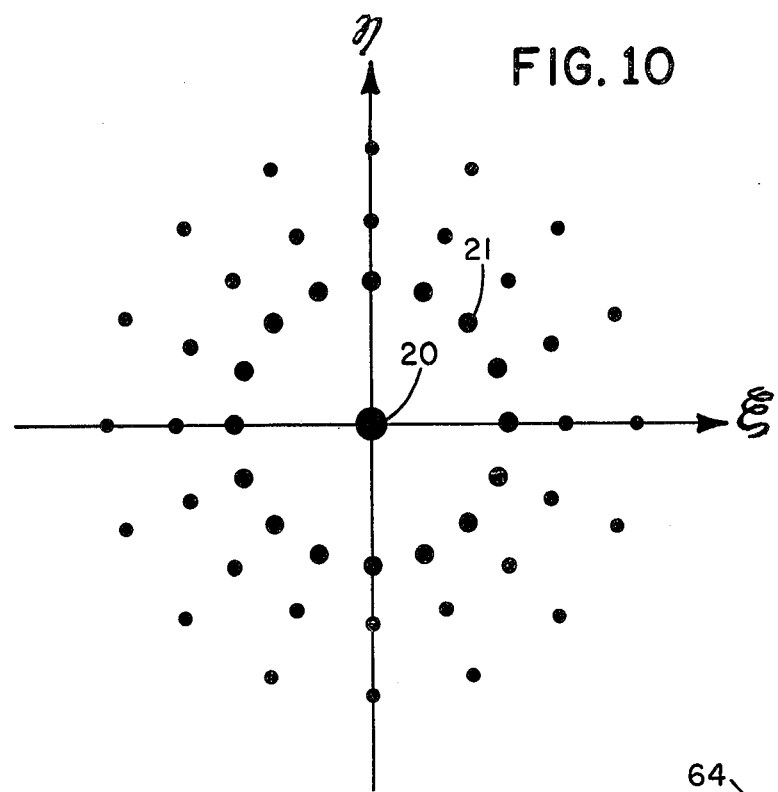
FIG. 10 shows a plan view of a diffraction image pattern formed by Fourier transformation of the periodic pattern rotated with the mesh plate shown in FIG. 2.

Spatial filter 26 always prevents the transmission of the first and higher order diffraction light even if mesh plate 11 is rotated and shifted. When mesh plate 11 is rotated by rotating mechanism 40, the Fourier transformed pattern shown in FIG. 4 is rotated as shown in FIG. 10. As shown in FIG. 10, the first order diffraction areas 21 form a ring about the zeroth order diffraction area 20 and the higher order (more than second order) diffraction areas form rings outside the first order diffraction areas 21. Also, when mesh plate 11 is shifted in a direction orthogonal to the optical path of the coherent light, the Fourier transformed pattern shown in FIG. 4 does not change. Therefore, spatial filter 26 always prevents the transmission of the first and higher order diffraction light even if mesh plate 11 is rotated or shifted. Thus, it is not required to precisely align the spatial filter with the mesh plate if spatial filter 26 shown in FIG. 7 is used.

As mentioned with respect to FIG. 8, the light passed through mesh plate 11 is Fourier transformed by lens 35. Although the periodic pattern in FIG. 8 transmits light, the invention also is applicable to periodic patterns which reflect light. FIG. 11 shows an embodiment of the invention for light reflective surfaces where like reference numerals are used to designate like portions in FIG. 8. Because of the light reflecting nature of the periodic pattern, a beam splitter 44 is disposed between lens 35 and object 46. The coherent light beam passes through collimator 31 and is reflected by beam splitter 44 to impinge against a light reflecting object having a periodic pattern. The light reflected from object 46 is directed toward lens 35 through beam splitter 44 to enable the apparatus to detect defects in the periodic pattern.

Figure 12:
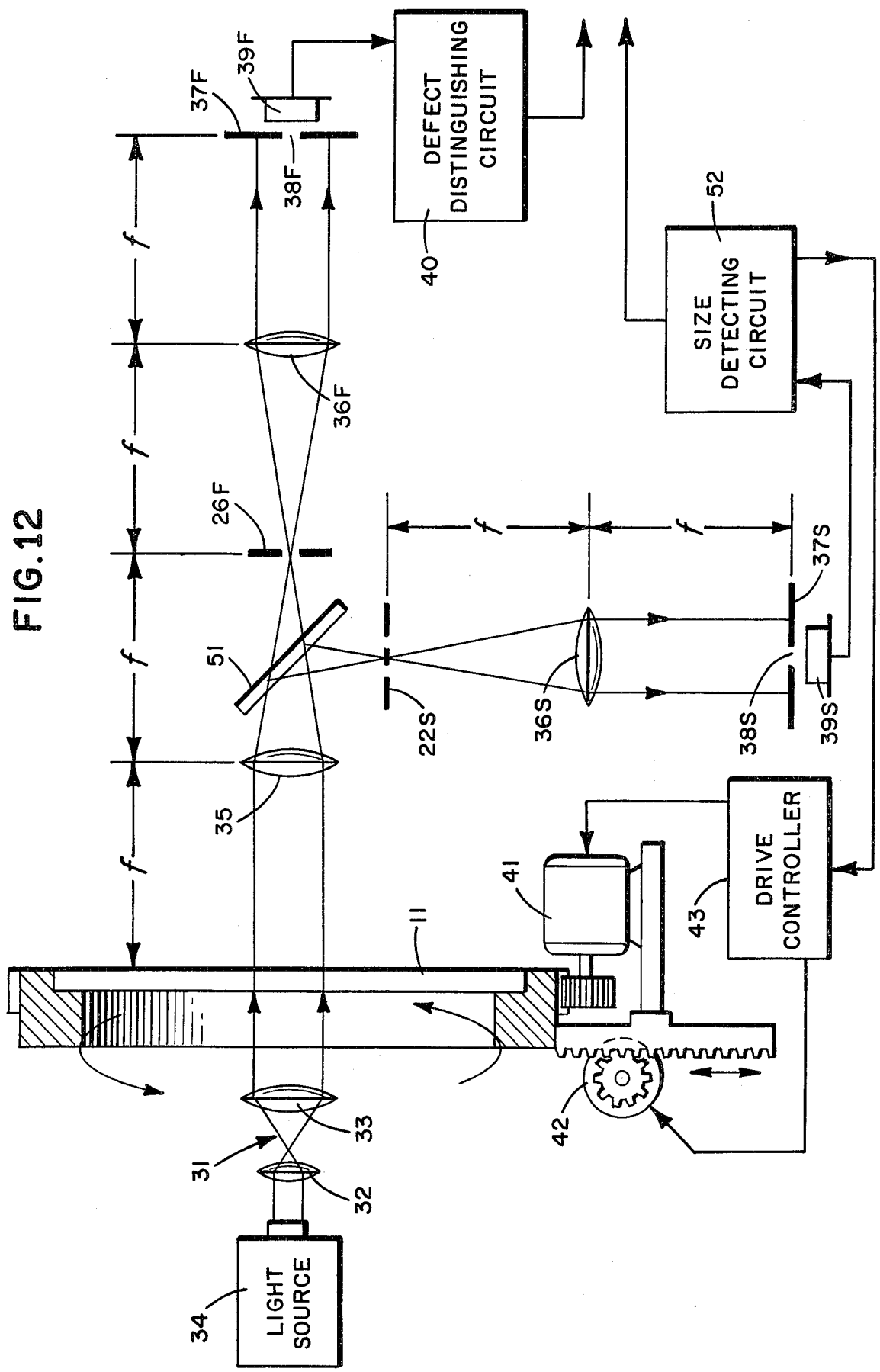
FIG. 12 shows a schematic diagram of a further embodiment of the invention.

FIG. 12 shows another embodiment of this invention which detects the size of the defects. Again like reference numerals are used to designate like portions in FIG. 8. The light beam is Fourier transformed by lens 35 and split into a first and second light beam by a beam splitter 51. The first light beam passes through a first spatial filter 26F which has a light blocking area for preventing the transmission of the first and higher order diffraction light and a circular light transmission area for passing the zeroth order diffraction light and the defect information light component. The light passed through spatial filter 26F is inverse Fourier transformed by lens 36F. The light passed through lens 36F is directed through a pinhole 38F in screen 37F to photo-electric converter 39F.

On the other hand, the second spatial filter 22S is the same as filter 22 in FIG. 6 and it is positioned at the backward focal point of lens 35. The second spatial filter 22S has a light blocking area for blocking mainly the periodic pattern information light component and a ring-like light transmission area for passing the defect information light component. The light blocking area of spatial filter 22S includes a spot-like light blocking area which prevents the transmission of the zeroth order diffraction light and another light blocking area which is disposed around the spot-like blocking area to prevent the transmission of the first and higher order diffraction light.

The light passed through the second spatial filter 22S is inverse Fourier transformed by a lens 36S. The light passed through second lens 36S then is directed through a pinhole 38S in screen 37S to photo-electric converter 39S. The photo-electric converter 39S is connected to a size detecting circuit 52. The electrical signal generated by the photo-electric converter 39S corresponds to the intensity of the received light.

Figure 13:
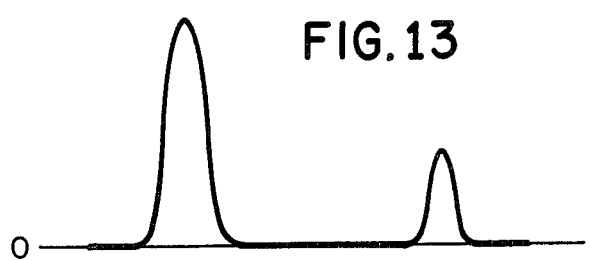
FIG. 13 shows waveforms obtained by photo-electric converter 39S shown in FIG. 12.

The electrical signal generated by photo-electric converter 39S does not contain a direct current component as shown in FIG. 13 because second spatial filter 22S prevents the transmission of the zeroth order diffraction light. The amplitude of the electrical signal is porportional to the size of the defect in the periodic pattern. Therefore, size detecting circuit 52 detects the size of the defect in the periodic pattern by sensing the amplitude of the electrical signal from the photo-electric converter 39S.

If the size of pinhole 38 is large, much light is received by photo-detector 39S. Therefore, rapid defect inspection is possible by using screen 37S with a larger pinhole 38S. Accordingly, at first, mesh plate 11 is scanned by the coherent light beam at rapid speed. When a defect is detected by size detecting circuit 52, a speed control signal is supplied to drive controller 43. Then, mesh plate 11 is scanned at slow speed to determine the kind of defect by defect distinguish circuit 40. Thus, in the embodiment shown in FIG. 12, it is possible to quickly determine the size and kind of defect.

In the embodiment shown in either FIG. 8 or FIG. 12, if a dichroic mirror is disposed between lens 32 and lens 33, and a gelatine filter is used as spatial filter 26F, and an incoherent light beam such as green light is projected to the dichroic mirror, a defect pattern can be designated by coherent light, such as red laser light, and a periodic pattern can be designated by the incoherent green light at the position of screen 37F.

FIG. 14 shows another embodiment of the invention. Unlike the apparatus shown in FIG. 8, the apparatus of FIG. 14 obtains information about a Fourier transformed image of a periodic pattern without using an optical system and calculates defect information from the information from the image information by arithmetic operations. More specifically, a light source 61 emits inchoherent light, which is applied through a lens 62 onto a periodic pattern 63. The light which passes through the pattern 63 forms a periodic pattern image 64 of a predetermined area. Periodic pattern image 64 is sampled by an image pickup device 65 and converted into electrical analog image signals. The analog image signals are supplied to an analog digital converter 66 and are converted into digital image signals. The digital image signals are stored in a two-dimensional memory 67 which can store $n \times n$ digital signals. That is, the periodic pattern image 64 is split by image pickup device 65 into $n \times n$ pixells, the pixells are converted into digital signals, and the digital signals are stored at predetermined addresses in the memory 67.

Figure 16:
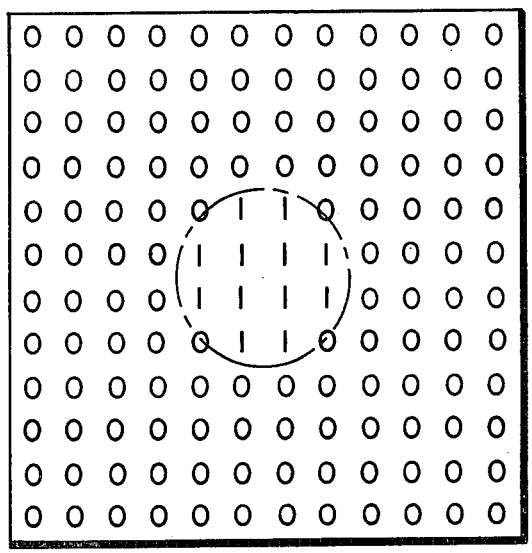
FIG. 16 shows filtering function data stored in a filtering function memory 72 shown in FIG. 14.

The digital image signals are read out from two-dimensional memory 67 and undergo a Fourier transform operation by a Fourier transformer 68. The signals from Fourier transformer 68 are then stored in a two-dimensional memory 69. Fourier transformer 68 may be the AP-400 which is made by ANALGIC, Inc. and which achieves a high speed Fourier transformation. The signals are read out from two-dimensional memory 69 and then multiplied one after another by a multiplier 70. Only defect signals from these signals are stored in a memory 71. The multiplication at multiplier 70 is carried out according to filtering function data stored in filtering function memory 74; this takes out only the defect component signals. As shown in FIG. 16, the filtering function data consists of $n \times n$ digital data. The area filled with digit numerals "0" correspond to a light blocking area as illustrated in FIG. 7, and the area filled with digit numerals "1" corresponds to a light transmission area. In other words, the filtering function data is a pattern formed of digital signals which correspond to $n \times n$ pixells defining the image of the spatial filter 26 of FIG. 7. The number of pixells which corresponds to the diameter of the light transmission area of FIG. 7 is expressed as $2\lambda f/P(1-1/N)$.

The defect signals read out from the memory 71 are supplied to an inverse Fourier transformer 72. These signals undergo an inverse Fourier transformation and are converted into pixell digital signals which represent a defect image. The inverse Fourier transformer 72 may be of the same type as Fourier transformer 68. The pixell digital signals thus obtained are supplied to a digital-analog converter 73 and thus converted into analog defect image signals. The apparatus of FIG. 14, though not provided with an optical system, thus can distinguish the kind of defect.

Figure 15:
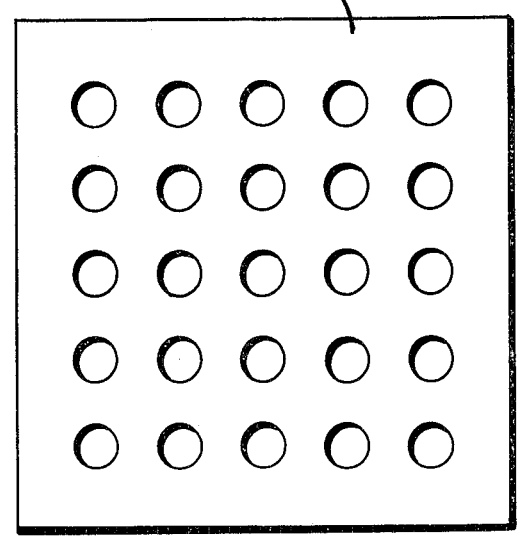
FIG. 15 shows a plan view of a periodic pattern image obtained by the apparatus shown in FIG. 14.

Although the periodic patterns shown in FIGS. 2 and 15 have holes arranged equidistantly, the holes of the pattern do not have to be arranged in this manner. For example, as in the pattern shown in FIG. 17, the distance from a hole 75 to an adjacent hole 76 is P1 and the distance from the hole 75 to an adjacent hole 77 is P2. These distances are not equal. Such a pattern can be used so long as the pattern is arranged periodically.

We claim:

1. In an apparatus for inspecting defects in a periodic pattern, an optical device comprising:
    a light source for directing a coherent light beam toward the periodic pattern;
    a Fourier transformer positioned to receive and transform the coherent light beam after it strikes the periodic pattern, said Fourier transformer generating a defect information light component and a periodic pattern information light component, the periodic pattern information light component including zeroth order diffraction light and first and higher order diffraction light; and
    filtering means positioned at the backward focal point of said Fourier transformer and having a light blocking area for blocking transmission of first and higher order diffraction light and a circular light transmission area for passing zeroth order diffraction light and the defect information light component.

2. In an apparatus for inspecting defects in a periodic pattern according to claim 1, said optical device further comprising: an inverse Fourier transformer positioned to receive and transform the light which passes through said circular light transmission area of said filtering means; and photo-electric converting means for sensing the intensity of the light which passes through said inverse Fourier transformer and generating electrical signals.

3. In an apparatus for inspecting defects in a periodic pattern according to claim 1, said optical device further comprising shifting means for shifting the periodic pattern in a direction orthogonal to an optical path of the coherent light beam and rotating means for rotating the periodic pattern in a plane normal to the optical path of the coherent light beam.

4. In an apparatus for inspecting defects in a periodic pattern according to claim 1, wherein the periodic pattern has a mesh like configuration which transmits light.

5. In an apparatus for inspecting defects in a periodic pattern according to claim 1, wherein the periodic pattern is light reflective.

6. An apparatus for inspecting defects in a periodic pattern comprising:
    a light source for directing a coherent light beam toward the periodic pattern;
    a Fourier transformer positioned to receive and transform the coherent light beam after it strikes the periodic pattern, said Fourier transformer generating a defect information light component and a periodic pattern information light component, the periodic pattern information light component including zeroth order diffraction light and first and higher order diffraction light;
    filtering means positioned at the backward focal point of said Fourier transformer and having a light blocking area for blocking transmission of first and higher order diffraction light and a circular light transmission area for passing zeroth order diffraction light and the defect information;
    an inverse Fourier transformer positioned to receive and transform light which passes through said circular light transmission area of said filtering means;
    photo-electric converting means for sensing the intensity of the light which passes through said inverse Fourier transformer and generating electrical signals; and
    defect distinguishing means connected to said photoelectric converting means for distinguishing the kind of defect in the periodic pattern by determining the amplitude of the electrical signals generated by said photo-electric converting means.

7. In an apparatus for inspecting defects in a periodic pattern, the combination comprising:
  a light source for directing a coherent light beam toward the periodic pattern;
  a Fourier-transformer positioned to receive and transform the coherent light beam after it passes through the periodic pattern, said Fourier transformer generating a defect information light component and a periodic pattern information light component, the periodic pattern information light component including zeroth order diffraction light and first and higher order diffraction light;
  a beam splitter for splitting the light which passes through said Fourier transformer into a first and second light beam;
  first filtering means positioned to receive the first light beam from said beam splitter, said first filtering means having a light blocking area for blocking transmission of first and higher order diffraction light and a circular light transmission area for passing the zeroth order diffraction light and the defect information light component;
  a first inverse Fourier transformer positioned to receive and transform the light which passes through said circular light transmission area of said first filtering means;
  second filtering means positioned to receive the second light beam from said beam splitter, said second filtering means having a light blocking area for blocking the periodic pattern information light component and a ring-like light transmission area for passing the defect information light component, said light blocking area of said second filtering means including a spot-like light blocking area which prevents transmission of the zeroth order diffraction light and a peripheral light blocking area disposed around said spot-like light blocking area to prevent transmission of the first and higher order diffraction light; and
  a second inverse Fourier transformer positioned to receive and transform the light which passes through said ring-like light transmission area of said second filtering means.

8. In an apparatus for inspecting defects in a periodic pattern according to claim 7, the combination further comprising:
  first photo-electric converting means for sensing the intensity of the light which passes through said first inverse Fourier-transformer and generating electrical signals;
  defect distinguishing means connected to said first photo-electric converting means for distinguishing the kind of defect in the periodic pattern by determining the amplitude of the electrical signals generated by said first photo-electric converting means;
  second photo-electric converting means for sensing the intensity of the light which passes through said second inverse Fourier transformer and generating electrical signals; and
  size detecting means connected to said second photo-electric converting means for detecting the defect size in the periodic pattern by determining the amplitude of the electrical signals of said second photo-electric converting means.

9. In an apparatus for inspecting defects in a periodic pattern according to claim 8, the combination further comprising:
  shifting means for shifting the periodic pattern in a direction orthogonal to an optical path of the coherent light beam and rotating means for rotating the periodic pattern in a plane normal to the optical path of the coherent light beam.

* * * * *